(12) United States Patent
Ackelsberg et al.

(10) Patent No.: US 6,285,741 B1
(45) Date of Patent: Sep. 4, 2001

(54) METHODS AND APPARATUS FOR AUTOMATIC IMAGE NOISE REDUCTION

(75) Inventors: Sholom M. Ackelsberg, Brookfield; Gary R. Strong, Waukesha; Holly A. McDaniel, New Berlin; Carlos F. Guerra, Lake Mills; Hui Hu; Hui David He, both of Waukesha; Robert Senzig, Germantown, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/140,105

(22) Filed: Aug. 25, 1998

(51) Int. Cl.[7] .................................................. A61B 6/00
(52) U.S. Cl. ............................... 378/110; 375/16
(58) Field of Search .................. 378/4, 8, 15, 16, 378/19, 108, 109, 110

(56) References Cited

U.S. PATENT DOCUMENTS 5,018,178 * 5/1991 Katsumata ............................ 378/91
5,084,908 * 1/1992 Alberici et al. .......................... 378/4
5,228,070 * 7/1993 Mattson ................................ 378/19
5,262,946 * 11/1993 Heuscher ............................. 378/108
5,400,378   3/1995 Toth .
5,485,494 * 1/1996 Williams et al. ...................... 378/16

FOREIGN PATENT DOCUMENTS 0 404 118   12/1990 (EP) .

* cited by examiner

*Primary Examiner*—David P. Porta
(74) *Attorney, Agent, or Firm*—Armstrong Teasdale LLP; Christian G. Cabou

(57) ABSTRACT

The present invention, in one form, is a system which, in one embodiment, adjusts the x-ray source current to reduce image noise to better accommodate different scanning parameters. Specifically, in one embodiment, the x-ray source current is adjusted as a function of image slice thickness, scan rotation time, collimation mode, table speed, scan mode, and filtration mode. Particularly, a function is stored in a CT system computer to determine an x-ray source current adjustment factor so that the appropriate x-ray source current is supplied to the x-ray source for the determined parameters. After adjusting the x-ray source current, an object is scanned.

27 Claims, 4 Drawing Sheets

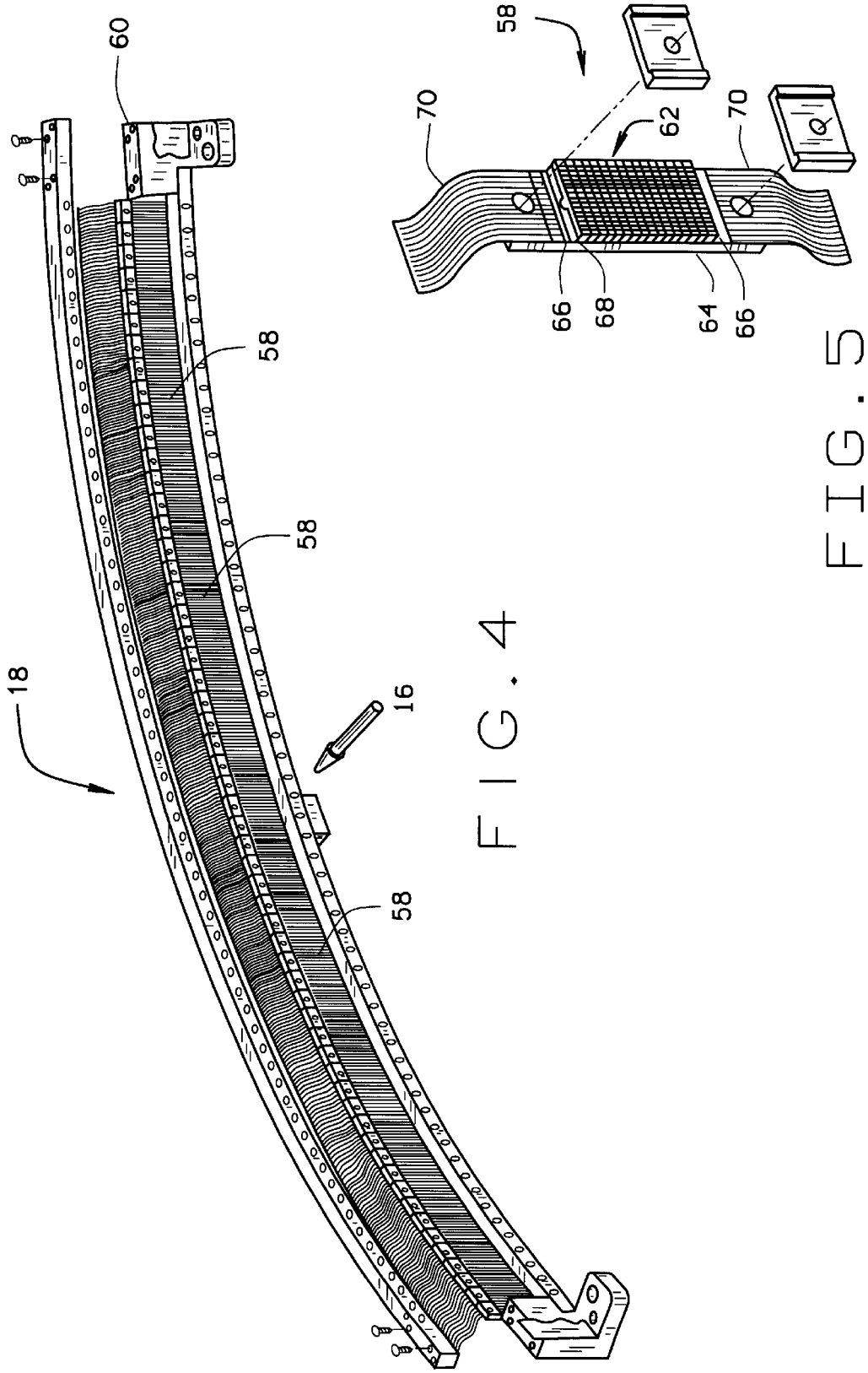

METHODS AND APPARATUS FOR AUTOMATIC IMAGE NOISE REDUCTION

BACKGROUND OF THE INVENTION

This invention relates generally to computed tomography (CT) imaging and more particularly, to automatically adjusting x-ray source current to reduce image noise in a CT system.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Detector element of the array produce a separate electrical signal that is a measurement of the beam attenuation at the detector location. The attenuation measurements from all the detectors are acquired separately to produce a transmission profile.

In known third generation CT systems, the x-ray source and the detector array arc rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Certain scanning parameters, such as scan rotation speed, image slice thickness, scan mode, x-ray collimation, filtration, and table speed are known to affect required x-ray source current ("mA"), which relates directly to image noise. In order to optimize image noise, for example, a faster rotation typically requires a higher x-ray tube current level. Conversely, slower rotation typically requires a lower x-ray source current level. Similarly, a thinner image typically requires a higher x-ray source current level as compared to a thicker image.

To optimize image noise, known CT systems require an operator to consider each operating parameter to determine the appropriate x-ray source current. Specifically, in determining the x-ray tube current, the operator must consider each of the operating parameters as well as the interrelationship of each parameter. The possibilities created by the interrelationships may lead to operator confusion causing the operator to incorrectly determine the x-ray source current. As a result, either image quality is reduced or the patient may be exposed to increased x-ray dosages as a result of the incorrect x-ray current.

Accordingly, it would be desirable to provide an algorithm to facilitate optimizing image noise based upon the operating parameters of the imaging system. It also would be desirable for such algorithm to facilitate reducing x-ray dosage by matching image quality requirements and x-ray source current.

BRIEF SUMMARY OF THE INVENTION

These and other objects may be attained in a system which, in one embodiment, adjusts an x-ray source current to reduce image noise and improve image quality for different scanning operating parameters. Specifically, in one embodiment, an operator determines operating parameters of an imaging system. Based upon the determined operating parameters, an adjusted x-ray source current factor is generated. The adjusted x-ray source current factor is utilized to adjust the current to the x-ray source to automatically optimize image noise.

More particularly and in an exemplary embodiment, prior to a scan, the operator determines the operating parameters of the imaging system. The x-ray source current adjustment factor is determined as a function of image slice thickness, scan rotation time, collimation mode, table speed, scan mode, and filtration mode parameters as determined by the operator via a user interface. The appropriate x-ray source current is then determined using the x-ray source current adjustment factor so that the image noise is automatically optimized for the determined parameters. In other embodiments, the operator may select pre-defined preferences to determine the adjusted x-ray source current level.

By adjusting the x-ray source current as described above, image noise is optimized for a plurality of scanning parameters. In addition, the x-ray source current is determined in accordance with a defined function so that possibility of erroneous settings of x-ray source current is substantially reduced.

BRIEF DESCRIPTION OF THE DRAWINGS

FIG. 4 is a perspective view of a CT system detector array.

FIG. 5 is a perspective view of a detector module.

DETAILED DESCRIPTION OF THE INVENTION

Figure 1:
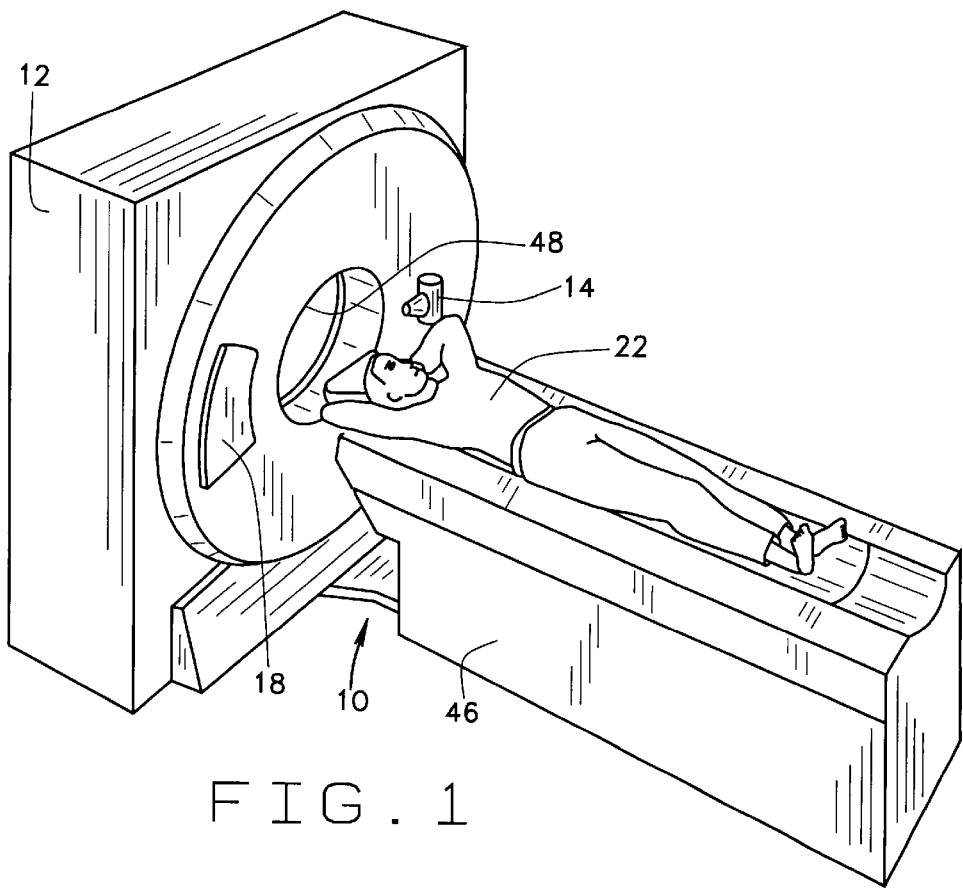
FIG. 1 is a pictorial view of a CT imaging system.
Figure 2:
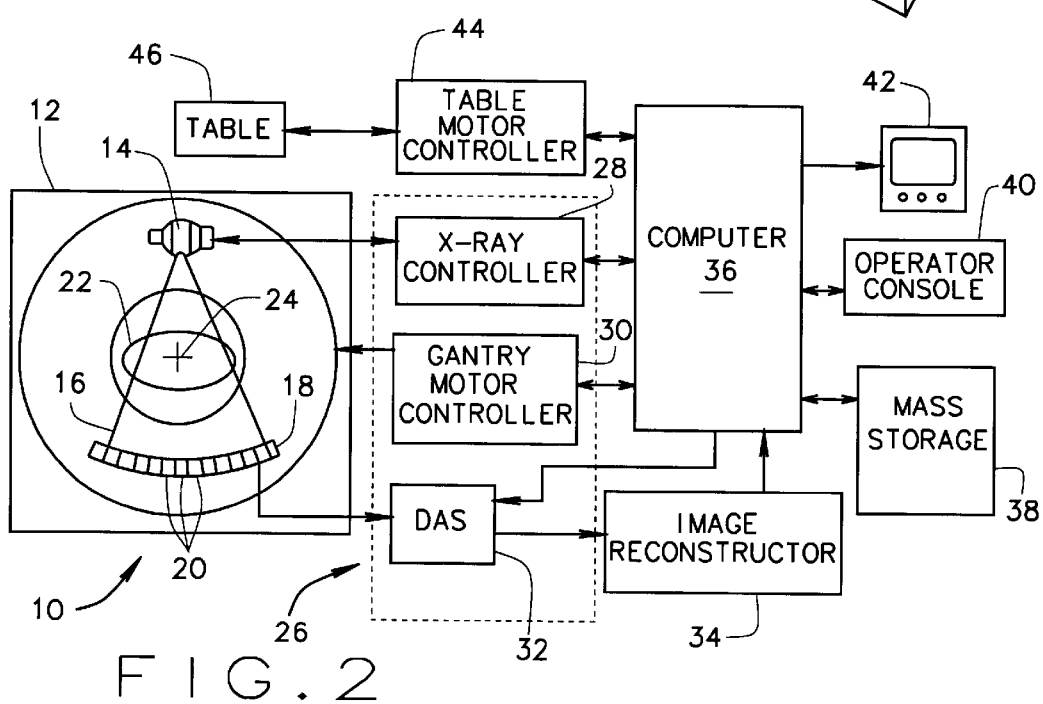
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signal for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives and supplies signals via a user interface, or graphical user interface (GUI). Specifically, computer receives commands and scanning parameters from an operator via console 40 that has a keyboard and a mouse (not shown). An associated cathode ray tube display 42 allows the operator to observe the reconstructed image and other data from computer 36. The operator supplied commands and parameters are used by computer 36 to provide control signals and information to x-ray controller 28, gantry motor controller 30, DAS 32, and table motor controller 44.

While the present x-ray source current algorithm is described in accordance with a multislice system, the present invention is not limited to practice in any particular CT system, including a single slice system, nor is such current adjustment limited to any particular image reconstruction algorithm. Similarly, the present current adjustment is not limited to use in connection with any particular scan type such as helical and axial scans. It should be further understood that the current adjustment algorithm could be implemented, for example, in a separate host computer (not shown) to exchange signals and data with computer 36 and/or other components of system 10, for example, x-ray controller 28, gantry motor controller 30, DAS 32, and table motor controller 44 (FIG. 2).

Figure 3:
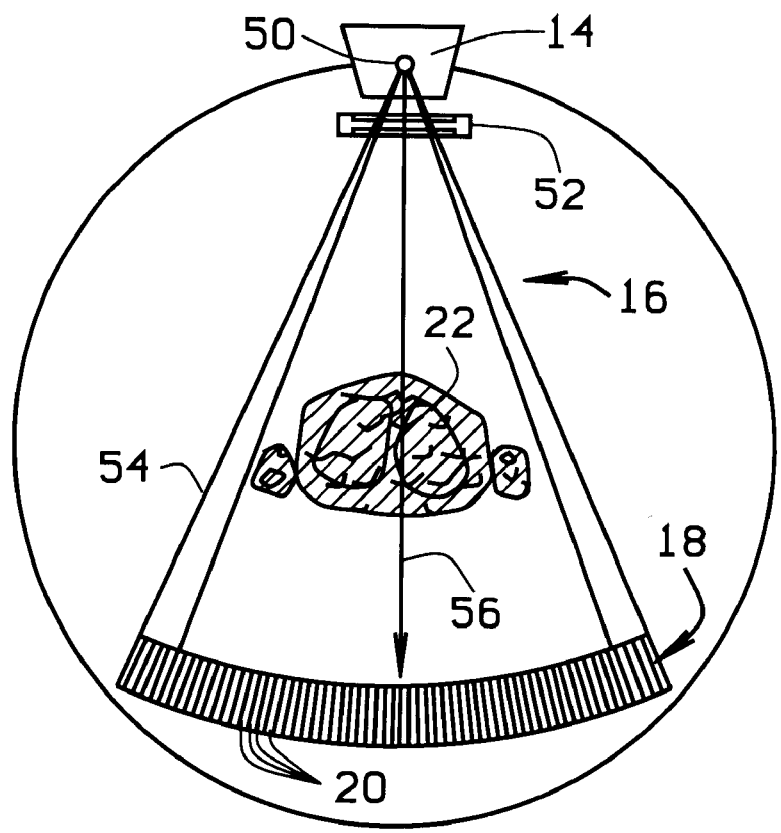
FIG. 3 is a schematic view of the CT imaging system with a pre-patient collimator.

Referring to FIG. 3, and with respect to operation of x-ray source 14, x-ray beam 16 emanates from a focal spot 50 of source 14. X-ray beam 16 is collimated by pre-patient collimator 52, and a collimated beam 54 is projected toward detector array 18 along a fan beam axis 56 centered within beam 16.

As shown in FIGS. 4 and 5, detector array 18 includes a plurality of detector modules 58. Each detector module 58 is secured to a detector housing 60. Each module 58 includes a multidimensional scintillator array 62 and a high density semiconductor array (not visible). A post patient collimator (not shown) is positioned over and adjacent scintillator array 62 to collimate scattered x-ray beams before such beams impinge upon scintillator array 62. Scintillator array 62 includes a plurality of scintillation elements arranged in an array, and the semiconductor array includes a plurality of photodiodes (not visible) arranged in an identical array. The photodiodes are deposited, or formed on a substrate 64, and scintillator array 62 is positioned over and secured to substrate 64.

Detector module 20 also includes a switch apparatus 66 electrically coupled to a decoder 68. Switch apparatus 66 is a multidimensional semiconductor switch array of similar size as the photodiode array. In one embodiment, switch apparatus 66 includes an array of field effect transistors (not shown) with each field effect transistor (FET) having an input, an output, and a control line (not shown). Switch apparatus 66 is coupled between the photodiode array and DAS 32. Particularly, each switch apparatus FET input is electrically connected to a photodiode array output and each switch apparatus FET output is electrically connected to DAS 32, for example, using flexible electrical cable 70.

Decoder 68 controls the operation of switch apparatus 66 to enable, disable, or combine the outputs of the photodiode array in accordance with a desired number of slices and slice resolutions for each slice. Decoder 68, in one embodiment, is a decoder chip or a FET controller as known in the art. Decoder 68 includes a plurality of output and control lines coupled to switch apparatus 66 and computer 36. Particularly, the decoder outputs are electrically connected to the switch apparatus control lines to enable switch apparatus 66 to transmit the proper data from the switch apparatus inputs to the switch apparatus outputs. The decoder control lines are electrically connected to the switch apparatus control lines and determine which of the decoder outputs will be enabled. Utilizing decoder 68, specific FETs within switch apparatus 66 are enabled, disable, or combined so that specific outputs of the photodiode array are electrically connected to CT system DAS 32. In one embodiment defined as a 16 slice mode, decoder 68 enables switch apparatus 66 so that all rows of photodiode array 52 are electrically connected to DAS 32, resulting in 16 separate, simultaneous slices of data being sent to DAS 32. Of course, many other slice combinations are possible.

In one specific embodiment, detector 18 includes fifty-seven detector modules 58. The semiconductor array and scintillator array 62 each have an array size of 16×16. As a result, detector 18 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 18 may be operated in many different slice thickness and number modes, e.g., one, two, and four slice modes. For example, the FETs can be configured in the four slice mode, so that data is collected for four slices from one or more rows of the photodiode array. Depending upon the specific configuration of the FETs as defined by decoder control lines, various combinations of outputs of the photodiode array can be enabled, disabled, or combined so that the slice thickness may, for example, be 1.25 mm, 2.5 mm, 3.75 mm, or 5 mm. Additional examples include a single slice mode including one slice with slices ranging from 1.25 mm thick to 20 mm thick, and a two slice mode including two slices with slices ranging from 1.25 mm thick to 10 mm thick. Additional modes beyond those described are possible.

Figure 6:
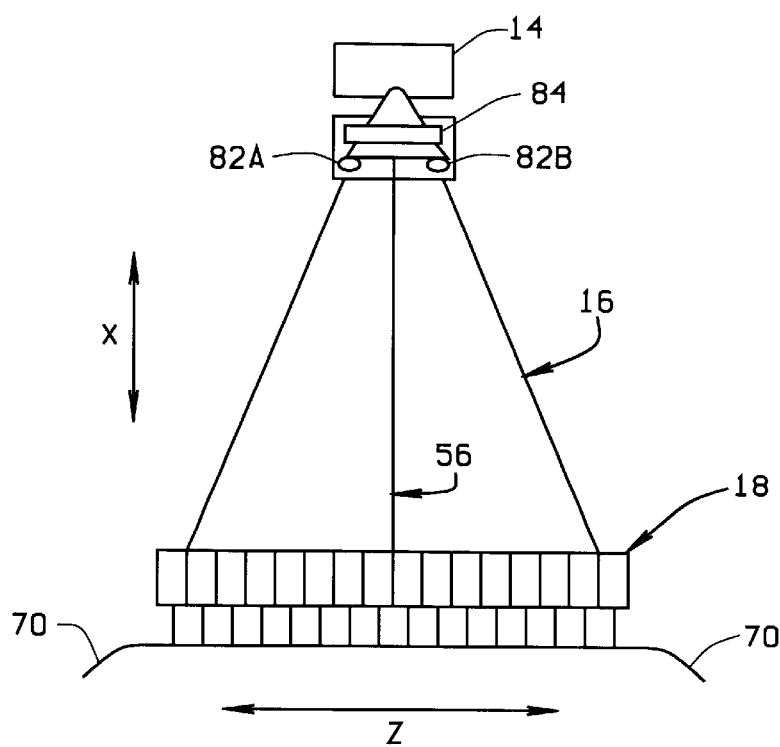
FIG. 6 is a schematic illustration of x-ray generation and detector components viewed from a side of the gantry.

In one embodiment and as shown in FIG. 6, illustrating a schematic illustration of system 10 viewed from a side of gantry 12, collimator 52 includes eccentric cams 82A and 82B, and a filtration device 84. The position of cams 82A and 82B are controlled by x-ray controller 28. Cams 82A and 82B are positioned on opposing sides of fan beam axis 56 and may be independently adjusted with respect to the spacing between cams 82A and 82B and their location relative to fan beam axis 56. Cams 82A and 82B may be positioned with a single cam drive, or alternatively, each cam may be positioned with a separate cam drive. Cams 82A and 82B are fabricated from an x-ray absorbing material, for example, tungsten and are coupled to the cam motors utilizing accurate ball bearings (not shown). As a result of the eccentric shape, the rotation of respective cams 82A and 82B alters the slice thickness of x-ray beam 16.

Figure 7:
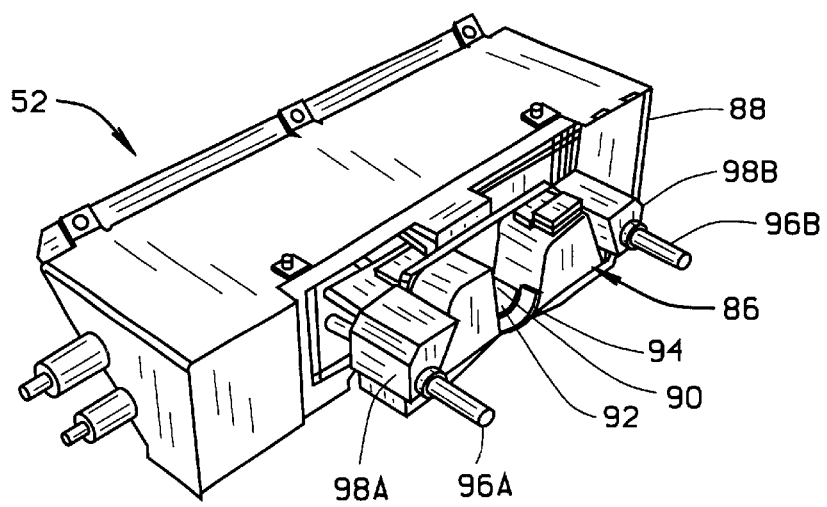
FIG. 7 is a perspective illustration of the collimator illustrated in FIG. 3.

As shown in FIG. 7, pre-patient collimator 52 further includes a movable filtration device 86, a housing 88, and a filter drive, or filter motor 90 for altering the position of filtration device 86 relative to housing 88. Specifically and in one embodiment, filtration device 86 includes a first filter 92 and a second filter 94. Filters 92 and 94 are positioned so that x-ray beam 16 projects through respective filters 92 and 94. Altering the position of filtration housing 86 modifies, or alters, the dosage of x-ray beam received by patient 22 by changing location of filtration device 86, specifically, the position of filters 92 and 94. For example, filters 92 and 94 may be combined in one of four combinations to alter x-ray beam 16. Specifically and in one embodiment, filters 92 and 94 may be positioned in a calibration mode, a body region mode, a head mode, or a block mode. These modes are defined by the amount of x-ray beam 16 that is allowed to pass through filters 92 and 94 as a function of location.

In operation and in accordance with one embodiment of the present invention, image noise of CT system 10 is automatically reduced or optimized by adjusting an x-ray current supplied to x-ray source 14. The adjusted x-ray source current is based on scanning operating parameters of system 10. In one embodiment, the scanning parameters include an image slice thickness, scan rotation time, collimation mode, table speed, scan mode, and filtration mode. In addition, other known scanning parameters may be utilized to determine the proper x-ray source current.

More specifically and in one embodiment, an operator determines, or prescribes, at least one operating parameter of system 10 via console 40, specifically, the keyboard and/or the mouse. The operator supplied parameters are then used by computer 36 to generate an x-ray source current adjustment factor. Utilizing the x-ray source adjustment factor, computer 36 supplies the appropriate control signals and information to x-ray controller 28, gantry motor controller 30, DAS 32, and table motor controller 44. Particularly, utilizing the mouse and/or the keyboard, the operator determines the image slice thickness, scan rotation time, collimation mode, table speed, scan mode, and filtration mode. Utilizing a function stored in a memory of computer 36, the x-ray current source adjustment factor is determined. The function may be a linear function so that the x-ray current is adjusted directly, or proportionally in accordance with the determined scanning parameters or may be a non-linear function so that different parameters may effect the adjusted x-ray current source adjustment factor differently.

After determining the x-ray source current adjustment factor, an appropriate x-ray source current is determined and supplied by controller 28 to x-ray source 14 to automatically reduce, or optimize, the image noise. Specifically, utilizing the function stored in computer 36 and the current adjustment factor, the appropriate x-ray source current is determined so that the desired image noise is maintained and the operator is not required to determine the appropriate x-ray source current. In addition to reducing the possibility of erroneous settings of the x-ray source current, the function stored in computer 36 may be utilized to reduce patient dose by matching image quality requirements to source current.

For example in one embodiment, the operator may utilize the mouse to determine the scan rotation time is 0.8 seconds, the image thickness is 5 mm, the number of slices is 4, pre-patient collimation of 20 mm, the table speed is 30 mm per rotation, axial scan mode, and a body region filtration mode. As a result., computer 36 supplies the appropriate signals to x-ray controller 28, gantry motor controller 30, DAS 32 and table motor controller 44 so that system 10 is configured in accordance with the operator determined parameters. Patient, or object 22 is then scanned and slice data is collected using detector array 18. After collecting the slice data, a reconstructed image is generated using reconstructor 34 and displayed on cathode ray tube 42.

In other embodiments, pre-defined system parameters may be stored in computer 36 for use by the operator. The pre-defined parameters allow the operator to quickly select typical scans to be performed. In addition, utilizing the user interface, computer 36 may be configured so that additional or altered functions are stored in memory so that operator or user defined functions or preferences are created.

In another embodiment, default system scan parameters, i.e., slice thickness and x-ray source current, are based upon the defined scan protocol and preferences defined by an operator. If the operator makes changes to any of the default parameters, the remaining scan parameters are determined, or adjusted, to optimize the image noise. In determining the appropriate changes based on the modified scan parameters, certain parameters are given higher priority, or preference, so that those parameters remain unchanged, if possible. The remaining parameters are given lower priority so that these parameters are the first to be changed.

In operation, after the operator has selected a scan protocol, for example a head scan, a default setting for each scan parameter is provided. If, however, the operator adjusts one or more of the default parameters, the algorithm adjusts the remaining parameters using a parameter priority definition, or schedule. For example, if after selecting a head scan, the operator changes the pitch parameter, the algorithm will adjust the remaining parameters according to the priority definition. The parameter priority may, for a head scan, be such that the slice thickness is the highest priority, i.e., last parameter to be changed, to maintain image resolution. As a result, the remaining parameters are adjusted to the meet the modified scan protocol and optimize image noise. The high priority parameters are only adjusted if the defined scan cannot be performed without the adjustment of the high priority parameters. For example, in the head scan described above, the slice thickness is adjusted only if the defined scan cannot be completed without adjusting slice thickness. In addition, the priority parameters may include one or more of the scan parameters and may, for example, be stored in a scan prescription file in computer 36.

The above described algorithm facilitates automatic optimization of image noise for a plurality of scanning parameters. In addition, such algorithm substantially reduces the possibility of erroneous operator settings. Furthermore, the algorithm may be utilized to reduce patient dose by matching image quality requirements to x-ray source current.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. For example, the algorithm was described above in a static mode, however, the algorithm may be utilized dynamically during patient scanning. Additionally, the algorithm may be utilized with an x-ray system. Accordingly, the spirit and scope of the invention are to be limited only by the terms of the appended claims.

What is claimed is:

1. A method for optimizing image noise in an imaging system, the imaging system including an x-ray source and a detector, the detector including at least one slice of detectors, the imaging system providing default imagining system parameters for each of a plurality of scan protocols said method comprising;
   accepting a scan protocol selection,
   providing a plurality of pre-programmed default imaging system parameters for the selected scan protocol;
   accepting an adjustment of at least one default imaging system parameter;
   generating an x-ray source current adjustment factor dependent upon the at least one adjusted imaging system parametel using an algorithm stored in the imaging, system;
   statically adjusting an x-ray source current using the generated x-ray source current adjustment factor; and
   after adjusting the x-ray source current scanning an object using the statically adjusted x-ray source current.

2. A method in accordance with claim 1 wherein the plurality of pre-programmed imaging system parameters includes at least one of image slice thickness and a scan rotation time.

3. A method in accordance with claim 2 wherein the plurality of pre-programmed imaging system parameters further includes at least one of a collimation mode, a table speed, a scan mode, and a filtration mode.

4. A method in accordance with claim 1 further comprising collecting slice data using the detector.

5. A method in accordance with claim 4 wherein collecting slice data comprises collecting at least one slice of data.

6. A method in accordance with claim 4 wherein collecting slice data comprises collecting, multiple slices of data.

7. A method in accordance with claim 1 wherein accepting an adjustment of at cast one default imaging system parameter comprises accepting a parameter priority.

8. A method in accordance with claim 1 wherein generating an x-ray source current adjustment factor comprises applying a linear function to the adjusted imaging system parameters.

9. A method in accordance with claim 1 wherein generating an x-ray source current factor comprises applying a non-linear function to the adjusted imaging system parameters.

10. A method in accordance with claim 1 wherein generating an x-ray source current adjustment factor comprises utilizing a stored function to adjust the source current in accordance with image quality requirements.

11. A system for optimizing image noise in an imaging system tile imaging system including an x-ray source, a computer and a detector the detector including at least one slice of detectors said system configured to be coupled to the x-ray source and the computer to:
   accept a scan protocol selection;
   provide a plurality of pre-programmed default imaging system parameters for the selected scan protocol;
   accept an adjustment of at least one said default imaging system parameter;
   generate an x-ray source current adjustment factor based on said at least one adjusted imaging system parameter using a stored algorithm;
   statically adjust an x-ray source current using said generated x-ray source current adjustment factor; and
   after statically adjusting the x-ray source current, scan an object using said statically adjusted x-ray source current.

12. A system in accordance with claim 11 wherein to generate an x-ray source current adjustment factor, said system is configured to apply a linear function to the adjusted imaging system parameters.

13. A system in accordance with claim 11 wherein to generate an x-ray source current adjustment factor, said system is configured to apply a non-linear function to the adjusted imaging system parameters.

14. A system in accordance with claim 11 wherein said plurality of pre-programmed imaging system parameters includes at least one of image slice thickness and a scan rotation time to maintain desired image noise characteristics.

15. A system in accordance with claim 14 wherein said plurality of pre-programmed imaging system parameters includes at least one of a collimation mode, a table speed, a scan mode, and a filtration mode.

16. A system in accordance with claim 11 wherein said system is further configured to adjust an x-ray source current in accordance with image quality requirements.

17. An imaging system comprising:
   an x-ray source configured to project an x-ray beam;
   a detector array including an array of detectors configured to collect slice data; and
   a computer configured to:
      accept a scan protocol selection;
      provide a plurality of pre-programmed default imaging system parameters for the selected scan protocol;
      accept an adjustment of at least one default imaging system parameter; and
      generate an x-ray source current adjustment factor based on at least one adjusted imaging system parameter using a stored algorithm; and
   said imaging system configured to:
      statically adjust an x-ray source current of the x-ray source using the generated x-ray source current adjustment factor; and
      after statically adjusting the x-ray source current, scan an object using said statically adjusted x-ray source current.

18. An imaging system in accordance with claim 17 wherein said imaging system is further configured to adjust an x-ray source current in accordance with image quality requirements.

19. An imaging system in accordance with claim 17 wherein said slice data comprises at least one slice.

20. An imaging system in accordance with claim 17 wherein said slice data comprises data from multiple slices.

21. An imaging system in accordance with claim 17 wherein said computer comprises a memory and said default imaging system parameters are stored in said memory.

22. An imaging system in accordance with claim 21 wherein a scan priority function is stored in said memory to adjust said imaging system parameters.

23. An imaging system in accordance with claim 17 wherein said plurality of pre-programmed imaging system parameters comprise at least one of a slice thickness and a scan rotation time.

24. An imaging system in accordance with claim 23 wherein said plurality of pre-programmed imaging system parameters further comprise at least one of a table speed, an x-ray beam collimation mode, a scan mode, and an x-ray beam filtration mode.

25. An imaging system in accordance with claim 17 wherein said computer comprises a user interface configured to accept input from an operator to adjust said at least one default imaging system parameter.

26. An imaging system in accordance with claim 25 wherein said computer further comprises a memory and a linear function that is stored in said memory and used to generate said x-ray source current adjustment factor.

27. An imaging system in accordance with claim 25 wherein said computer further comprises a memory and a non-linear function that is stored in said memory and used to generate said x-ray source current adjustment factor.

* * * * *

UNITED STATES PATENT AND TRADEMARK OFFICE
CERTIFICATE OF CORRECTION

PATENT NO. : 6,285,741 B1  
DATED : September 4, 2001  
INVENTOR(S) : Ackelsberg et al.

It is certified that error appears in the above-identified patent and that said Letters Patent is hereby corrected as shown below:

Column 1,
Line 38, delete "that" and insert therefor -- the --.

Column 4,
Line 21, delete "disable" and insert therefor -- disabled --.

Column 5,
Line 64, delete "result.," and insert therefor -- result, --.

Column 6,
Line 35, delete "the".

Column 7,
Line 5, delete "imagining" and insert therefor -- imaging --.
Line 6, delete "protocols" and insert therefor -- protocols, --.
Line 7, delete "comprising;" and insert therefor -- comprising: --.
Line 15, delete "parametel" and insert therefor -- parameter --.
Line 16, delete "imaging," and insert therefor -- imaging --.
Line 19, delete "current" and insert therefor -- current, --.
Line 34, delete "collecting," and insert therefor -- collecting --.
Line 36, delete "cast" and insert therefor -- least --.
Line 51, delete "system tile" and insert therefor -- system, the --.
Line 52, delete "computer and a detector the" and insert therefor -- computer, and a detector, the --.
Line 53, delete "detectors" and insert therefor -- detectors, --.

Signed and Sealed this

Seventeenth Day of June, 2003

JAMES E. ROGAN  
*Director of the United States Patent and Trademark Office*